United States Patent [19]
Ashe et al.

[11] 4,096,389
[45] Jun. 20, 1978

[54] APPARATUS FOR MINIMIZING RADIATION EXPOSURE AND IMPROVING RESOLUTION IN RADIATION IMAGING DEVICES

[75] Inventors: John B. Ashe; Gwilym H. Williams, both of Palatine; Kenneth L. Sypal, Glen Ellyn, all of Ill.

[73] Assignee: G. D. Searle & Co., Chicago, Ill.

[21] Appl. No.: 684,641

[22] Filed: May 10, 1976

[51] Int. Cl.$^2$ .......................................... G01N 23/00
[52] U.S. Cl. ................................. 250/445 T; 250/505
[58] Field of Search ..................... 250/505, 445 T, 503

[56] References Cited
U.S. PATENT DOCUMENTS

| | | | |
|---|---|---|---|
| 1,551,162 | 8/1925 | Loebell | 250/505 |
| 2,760,077 | 8/1956 | Longini | 250/505 |
| 3,013,157 | 12/1961 | Norton | 250/505 |
| 3,778,614 | 12/1973 | Hounsfield | 250/505 |
| 3,814,938 | 6/1974 | Martone et al. | 250/505 |

*Primary Examiner*—Bruce C. Anderson
*Attorney, Agent, or Firm*—Dennis O. Kraft

[57] ABSTRACT

A collimator is disclosed for minimizing radiation exposure and improving resolution in radiation imaging devices. The collimator provides a penetrating beam of radiation from a source thereof, which beam is substantially non-diverging in at least one direction. In the preferred embodiment, the collimator comprises an elongated sandwich assembly of a plurality of layers of material exhibiting relatively high radiation attenuation characteristics, which attenuating layers are spaced apart and separated from one another by interleaved layers of material exhibiting relatively low radiation attenuation characteristics. The sandwich assembly is adapted for lengthwise disposition and orientation between a radiation source and a target or receiver such that the attenuating layers are parallel to the desired direction of the beam with the interleaved spacing layers providing direct paths for the radiation.

9 Claims, 13 Drawing Figures

APPARATUS FOR MINIMIZING RADIATION EXPOSURE AND IMPROVING RESOLUTION IN RADIATION IMAGING DEVICES

BACKGROUND OF THE INVENTION

This invention generally relates to radiation imaging devices and apparatus therefor and is particularly directed to the provision of a beam collimator which, while exhibiting utility in various radiological environments, is particularly useful in association with computer-assisted tomographic imaging equipment.

Radiographic imaging techniques and apparatus have undergone evolutionary advancement in recent years. By most accounts, the most promising development in the radiographic imaging field can be found in the provision and refinement of computer-assisted tomographic equipment and techniques which now enables the practitioner to non-invasively obtain detailed information relative to the location and condition of organs and other tissues within a patient's body, such information taking the form of a radiographic image of a thin cross-section or "slice" of the area of the body under consideration.

Previously, medical X-ray images have followed the basic radiographic process utilizing a stationary flat plate of film or a fluoroscopic screen fixed in place behind the patient. With this basic process, an X-ray source impinges upon the patient and the variable transmission of the X-ray beam through the patient is registered by radiation-sensitive material such as the film. This basic radiographic process has been and is now subject to certain disadvantages. Specifically, subtle differences occurring naturally in tissue radiation transmission and/or absorption cannot be detected due to the low sensitivity of the radiation-responsive imaging material, and due to scattered radiation of the X-ray beam while passing through the patient. Furthermore, and as can be appreciated, spatial or tomographic information cannot be obtained from such a basic radiographic process in that images of objects disposed in superposition to one another will confusingly overlap on the radiation-responsive material or film and, in many instances, be undetectable due to the inability of the material to distinguish between minor differences in radiological subject contrast.

A more advanced approach specifically calculated to provide spatial information involved efforts which were directed toward producing an in-focus image of a single preselected plane through an object by blurring out shadow images produced by structure on all planes except the preselected plane. This was typically accomplished by a combined motion of either the source and the recording medium or the object and the recording medium which rendered the shadow image from one plane only as a stationary image on the recording medium. Other efforts were directed toward the production of stereoscopic radiographs, again in an attempt to provide spatial information, and all as is well-documented in the literature. These efforts and processes have met with limited clinical success, and generally have not provided images of acceptable quality.

The development of computer-assisted tomography has eliminated most of the major problems and disadvantages associated with the prior art radiographic processes, so as to clearly reveal the internal organs and tissues of the body in cross-section instead of superimposed on one another, this tomographic technique utilizing a series of X-ray exposures made from different angles and taken axially through a "slice" or thin cross-sectional area of a patient. Specifically, in the computer-assisted tomographic process, a narrow X-ray or Gamma ray beam is transmitted transversely through a section of the patient anatomy and is detected by a high-efficiency radiation detector. A series of individual measurements of transmitted radiation is made about the subject so as to obtain multiple views of the "slice" in section. By virtue of these views, a large amount of information and data is acquired as to the differences in radiological subject contrast of the cross-section in question. This information or data constituting individual measurements at many angles about the subject then provides the input by which X-ray or Gamma ray attenuation coefficients can be calculated in a computer and the image of the cross-section of the patient anatomy actually reconstructed. Thus, a computer-assisted tomographic scanner obtains, by mathematical reconstruction, a transverse sectional image from transmitted radiation projection data, all as is well known.

Figure 1:
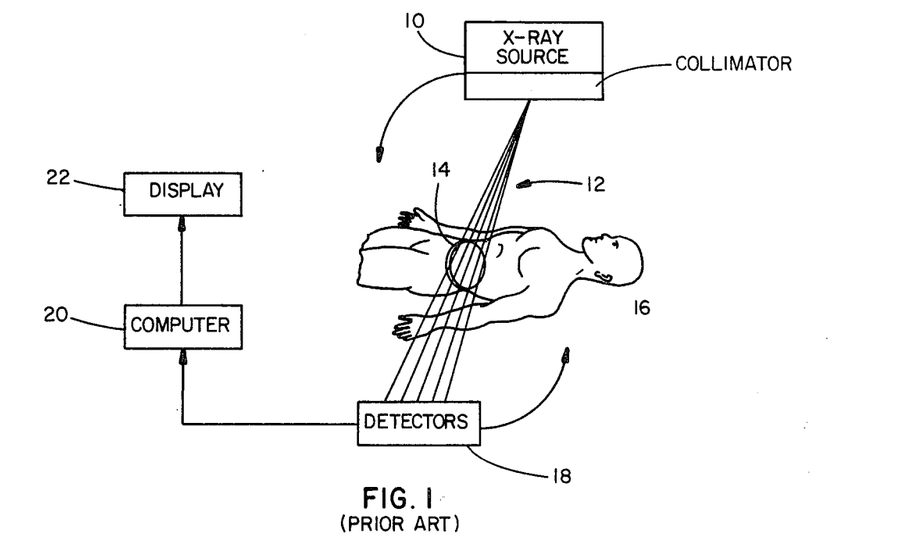
FIG. 1 is a schematic illustration of a typical conventional computer-assisted tomographic imaging device in which is illustrated the disposition of a collimator, such as would be constructed in accordance with the teachings of the instant invention.

From an apparatus standpoint, and as shown in FIG. 1 of the appended drawings, a computer-assisted tomographic system generally consists of the following basic components. A collimated X-ray source 10 is provided designed to ideally deliver a very narrow beam or beams of photons 12 through a "slice" 14 in a patient 16. Scintillation or gas detectors 18 are disposed opposite the collimated X-ray source 10. Relative motion between the collimated X-ray source 10, the scintillation or gas detectors 18, and/or the patient 16 is typically achieved by mounting the collimated X-ray source 10 and/or the detectors 18 on a movable rotatable gantry. Each detector responds to one pencil-like beam from the collimated X-ray source but, during rotation of the gantry, obtains a multiplicity of different and discrete data sets relative to the amount of attenuation of the X-ray beam while passing edgewise through the plane of interest 14 within the patient 16. This information then is fed to either a general-purpose programmed computer 20 or a special-purpose computer device whereat, through well-known mathematical algorithms, the image through the plane or cross-sectional slice 14 of the patient is reconstructed. The reconstructed image is subsequently read-out or displayed by a display device 22 such as a cathode-ray tube screen, printer, or the like.

From a theoretical viewpoint, computer-assisted tomographic scanning techniques are capable of producing a very finely resolved reconstructed image of the cross-sectional plane or "slice" in question. Practical and technological problems, however, detract from this theoretical possibility and, to date, images obtained through known computer-assisted tomographic scanning devices still do not provide desired levels of resolution.

One particularly important and significant problem associated with the known state-of-the-art is poor or blurred resolution of the reconstructed image caused by patient movement during the X-ray scan. In this respect, and so as to enable an adequate number of statistical photon events to be detected and subsequently evaluated, it oftentimes takes several minutes for a single scan to be effected of a cross-sectional plane or "slice" through the patient's body. During this time period, it is absolutely essential that the patient be motionless in that normal breathing, heartbeat, and other physiological effects produce a blurred image. A slow scan time, therefore, cannot avoid a certain deterioration in image quality. On the other hand, a fast scan time, one in which a complete scan is effected in a matter of seconds as opposed to minutes, generally is not yet a practical reality due to equipment limitations such as slow response times, dosage restraints, and the like.

For example, to provide a sufficient number of statistical events so as to enable reconstruction of an image with suitable resolution, a minimum number of photons is required to be delivered by an X-ray beam. If these photons must be delivered in a shorter as opposed to a longer period of time, then current equipment requires that the intensity of the radiation beam be increased. Yet, an increase in intensity of the radiation beam can provide an unacceptably high patient dose. A weaker intensity of impinging radiation, however, may not provide enough photons into the actual plane of interest to obtain meaningful information and may be such that the information obtained is lost due to the signal to noise ratio of the detectors.

A further problem concerns image degradation due to the effect of scattering in the area immediately surrounding the patient cross-section of interest. In this respect, prior-art devices have not been capable of limiting the beam only to the thin area of interest, and thus have had to contend with increased scattering, and with the delivery of unnecessary radiation to the patient.

Many of these problems could be avoided and a computer-assisted tomographic system can achieve high resolution of the image with a fast scanning rate and at low dosage through more careful control and collimation of the beam of emitted X-ray photons. Such beam should be extremely narrow and tightly collimated, and have a very narrow angle of divergence or beam spread such that virtually all of the photons emitted by the beam are directed through only the area of the "slice" and into an appropriate detector. Thus, not only would resolution be improved in that the maximum number of photons passing through a particular object within the cross-section of the patient would be received by the detector, noise due to scattered radiation outside the particular angle of view would be reduced and, very importantly, the radiation dosage to which the patient is subjected outside the thin plane of interest would be maintained at an absolute minimum.

To date, existing technology has not been able to supply a beam possessing these desirable characteristics and thus, the development of a "fast" computer-assisted tomographic imaging device exhibiting high resolution and minimizing radiation dosage to the patient has been retarded.

Part of the technological problem resides in the fact that X or Gamma rays cannot readily be focused electro-magnetically or by other means. The sources of such radiation are basically isotropic and the rays can generally be directed by geometric collimation techniques utilizing appropriate attenuating materials. However, standard collimation geometries conventionally available in the art and now utilized in conjunction with existing computer-assisted tomographic imaging devices by their nature result in diverging beams and thus in peripheral areas outside of the given "slice" or cross-section of interest of the patient being exposed to unnecessary radiation, increasing the risk to the patient and further degrading the information received during a diagnostic or analytic procedure by scattering from outside the region of interest into the sensing or detecting mechanisms, thereby causing a loss of resolution and possibly even providing erroneous data.

BRIEF SUMMARY OF THE INVENTION

It is therefore apparent that a need exists in this for the provision of a collimator which is capable of providing a penetrating beam of X or Gamma radiation from a source thereof, which beam is substantially non-diverging in at least one direction. It is the primary objective of the instant invention to provide such a collimator.

A further objective of the instant invention resides in the provision of a collimator apparatus which, when utilized in conjunction with a radiation imaging device, serves to provide the necessary minimal number of photons to insure adequate detected signals in a manner in which undesirable scattering is minimized and wherein an unacceptably high patient dose is avoided, irrespective of the scan rate in computer-assisted tomographic devices.

Still another objective of the instant invention is to provide a collimator apparatus which has general utility wherever a non-diverging beam of X or Gamma radiation is desired.

These objectives, as well as others which will become apparent as the description proceeds, are implemented by the instant invention which will be seen to comprise a collimator capable of providing a penetrating beam of X or Gamma radiation which is substantially non-diverging in at least one direction for particular though not exclusive utilization with radiation imaging devices such as computer-assisted tomographic apparatus. The collimator of the instant invention is simple in geometric design and, in its preferred form, comprises an elongated sandwich assembly of a plurality of layers of material exhibiting relatively high radiation attenuation characteristics, such as lead or tantulum, with these attenuating layers being spaced apart and separated from one another by interleaved layers of a material, such as air and/or acetate, which exhibits relatively low radiation attenuation characteristics.

An initial open aperture means is contemplated to be disposed between a source of radiation and the sandwich assembly constituting the collimator, the open aperture defining the boundary of the desired beam. The sandwich assembly is adapted for lengthwise disposition and orientation between the radiation source and a target or receiver such that the attenuating layers of the sandwich are parallel to the desired direction of the beam, with the interleaved spacing layers providing direct paths for the radiation.

Importantly, the radiation beam emerging from the sandwich assembly is substantially non-diverging in at least one desired direction. Thus, only the area of interest within an object such as a receiver or target will be irradiated by an imaging device utilizing the collimator of the instant invention, and deleterious scattering of radiation from areas outside the plane of interest is eliminated, thus improving resolution of the associated imaging device.

The particular pattern or shape of the beam produced can be varied by varying the geometry of the collimator. Specifically, if parallel beams are desired, the sandwich assembly will preferably comprise a plurality of sheets of substantially parallel layers of alternating attenuation material and spacing material, with each respective layer type being substantially uniform in length and in thickness, but with the thickness of the spacing layers being greater than the thickness of the attenuating layers to minimize attenuation of the beam in the desired direction. If a circular beam pattern is desired, the sandwich assembly could comprise a plurality of substantially equally spaced concentric cylindrical layers of alternating attenuation material and spacing material, with each respective layer being substantially uniform in length and in thickness. Alternatively, the circular beam pattern could be produced by providing a sandwich assembly which comprises a layer of attenuating material with the spacing layer being juxtaposed thereon, and with the assembly being rolled upon itself as a spiral.

Of criticality as concerns the construction of the collimator of the instant invention is that a plurality of thin layers of highly absorbing material be placed in the radiation beam parallel to the desired direction of the beam, with the thin layers of highly absorbing material being separated by or sandwiched between low absorbing material. Within this framework, numerous geometries can be provided, in that rays moving in the desired direction will pass through the layers of low absorption material, while diverging rays will always be required to pass through long geometric paths of multiple layers of high absorption material and thereby be highly attenuated.

BRIEF DESCRIPTION OF THE DRAWINGS

Further features and advantages of the invention will be understood and appreciated from the following detailed description of a preferred inventive embodiment, such description making reference to the appended sheets of drawings, wherein.

DETAILED DESCRIPTION OF THE PREFERRED INVENTIVE EMBODIMENT

As previously explained, since X or Gamma rays cannot readily be focused electro-magnetically or by other means, such radiation is generally directed by means of geometric collimation techniques utilizing appropriate attenuating material. Specifically, and as X or Gamma radiation passes through a material, attenuation of the radiation takes place with a resultant loss in beam intensity, such loss in intensity being represented by the following equation:

$$I = I_0 e^{-\mu x} \qquad 1$$

where $I_0$ is the intensity incident upon the attenuating material;

I is the beam intensity after passage through the material;

$\mu$ is the linear attenuation coefficient of the material; and x is the passage length through the material.

The attenuation coefficient $\mu$ is approximately proportional to the electron density of a given material and thus is low for materials of low atomic number and low mass density, and is high for high mass density and high atomic number materials. A typical material utilized in collimator design for attenuating X or Gamma radiation is therefore lead.

Figure 2:
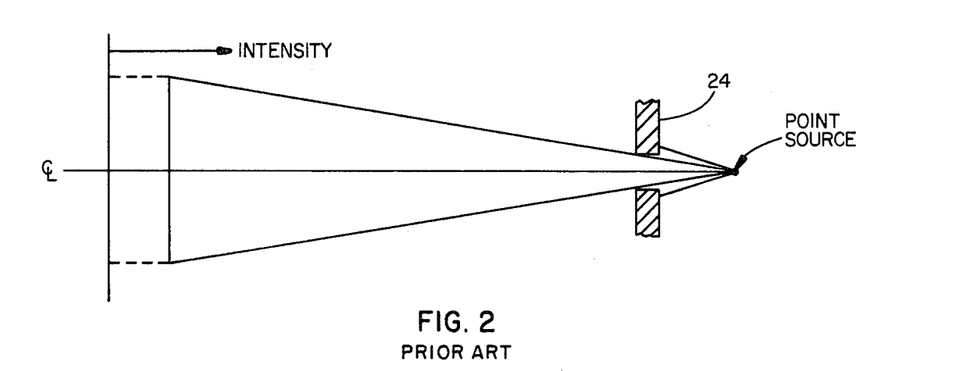
FIG. 2 is a schematic graphical representation depicting standard collimator geometry and the resulting beam intensity from a point source of radiation.

As is shown in FIG. 2, and assuming a point source of radiation, a simple prior art collimator might utilize a single aperture or slit in a material such as lead as represented by reference numeral 24. All radiation emitted from the point source in a direction which will not pass through the open aperture or slit impinges upon the collimator material and, depending upon the material characteristics and dimensions in accordance with the formulation set forth above, such improperly directed radiation is attenuated and absorbed. The basic principle of collimation, i.e. directing the rays only to a specific area or body of interest, therefore requires actual removal of unwanted rays, again bearing in mind that X or Gamma rays cannot be readily focused.

With reference again to FIG. 2 of the application drawings, radiation from the point source is directed to the target by being allowed to pass through the aperture as shown. Yet, with standard collimator designs, the resulting beam impinging upon the target has a radial divergence and thus it is quite difficult to control the actual beam width.

Figure 3:
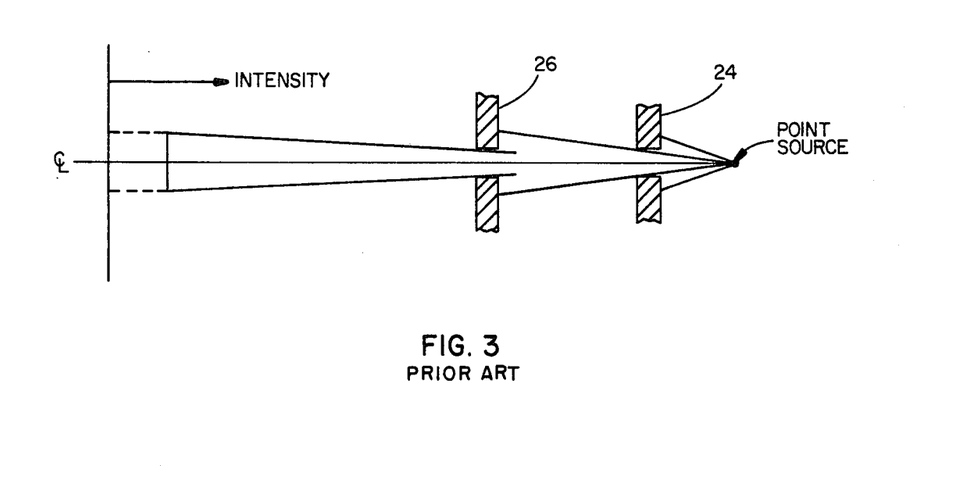
FIG. 3 is a schematic graphic representation of standard collimator geometry utilizing a double slit or extended slit aperture and depicting the resulting beam intensity, again from a point source of radiation.

In an effort to improve upon this situation, prior-art collimator approaches typically utilize a plurality of apertures as depicted in FIG. 3, such as an initial aperture in an attenuating material 24 and a second aperture in a further attenuating material 26. As is depicted, the divergence of the beam emitted by the point source of radiation when measured at the target is considerably narrower than is the case with a single aperture as is shown in FIG. 2. Nevertheless, wide beam divergence is still to be noted. Further, and as should be understood, the double aperture configuration of standard collimator designs as is depicted in FIG. 3 performs in much the same manner as would an extended slit collimator, i.e. one elongated in the direction of beam travel to form a channel or tube.

Figure 4:
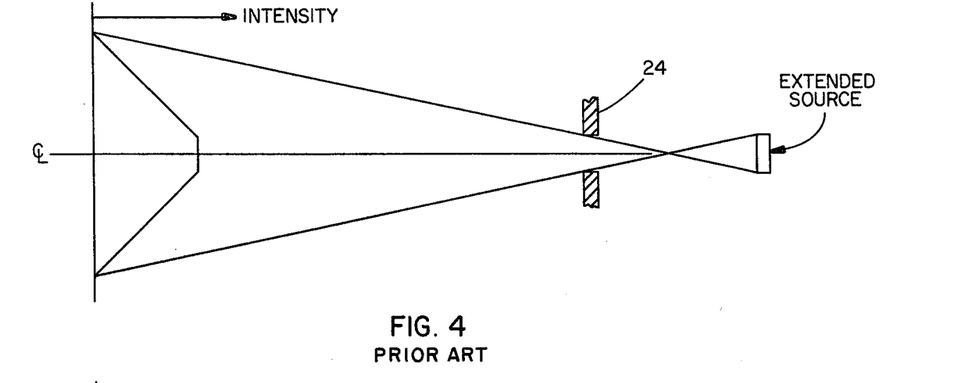
FIG. 4 is a schematic graphical representation again of standard collimator geometry utilizing a single collimator slit or aperture and depicting the resulting beam intensity from a line or extended radiation source.
Figure 5:
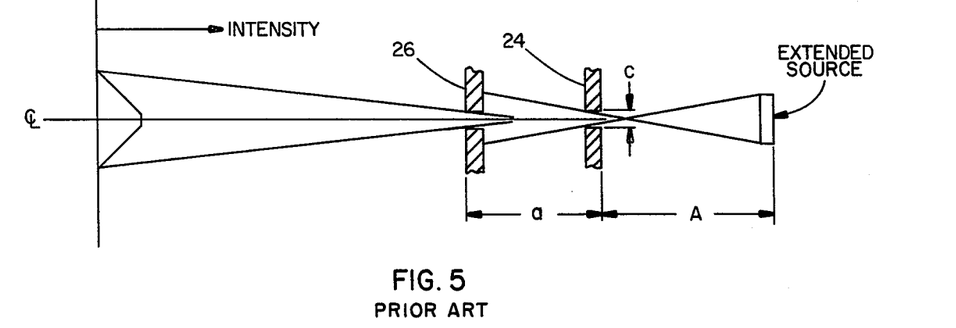
FIG. 5 is a schematic graphical representation of standard collimator geometry utilizing a double slit or an extended aperture and depicting the resulting beam intensity similarly from an extended or line source of radiation.

The discussion of standard collimator approaches as in FIG. 2 and FIG. 3 assumes the provision of a point source of radiation. In practice, however, radiation sources generally are not point sources but usually constitute line sources or extended sources in the fashion depicted in FIG. 4 and FIG. 5. With such extended or line sources, the problem of controlling divergence by collimation still exists and the projection of the rays from the source onto a target results in a falling off of intensity of the rays towards the geometrical boundaries of the beam. In FIG. 4, the resulting intensity of the beam is depicted from the utilization of a single slit aperture in a conventional collimator desing. FIG. 5, on the other hand, represents the resulting intensity wherein a double slit aperture or an extended or elongated slit is utilized.

In many environments of utility, such as in radiation imaging devices and particularly in computer-assisted tomographic apparatus, it is necessary to have a well collimated and a non-diverging radiation beam so that excessive radiation to the patient can be eliminated and the problem of resolution degradation caused by beam scattering can be markedly reduced. In other environments as well, a collimated and substantially non-diverging beam is particularly useful such as in the radiation of materials for examination of structure or composition, or for inducing chemical reaction at a target. The typical prior-art collimator designs which, in theory, are represented by the schematic illustrations of FIGS. 2 through 5 and the foregoing discussion, simply are not capable of producing the required substantially non-diverging beam.

Figure 6:
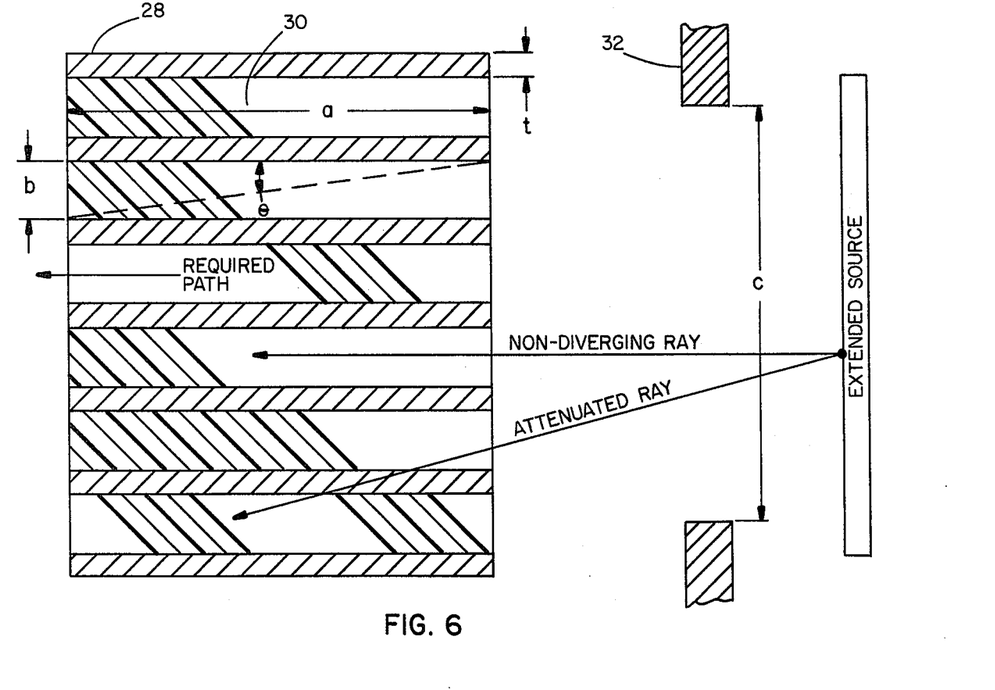
FIG. 6 is a schematic elevational view in section depicting the basic geometry of the collimator design of the instant invention.

This deficiency in the art is overcome by the provision of the collimator design of the instant invention, a schematic representation of which is shown in the elevational, sectional view of FIG. 6 of the application drawings.

With particular reference now to FIG. 6 of the drawings, a collimator design in accordance with the teachings of the instant invention is shown, this collimator providing a penetrating beam of X or Gamma radiation from the illustrated source thereof, such beam being substantially non-diverging in at least one direction. Specifically, the collimator will be seen to comprise an elongated, in the direction of beam travel, sandwich assembly of a plurality of layers of material 28, which material exhibits relatively high radiation attenuation characteristics, such attenuating material or layers 28 being spaced apart and separated from one another by interleaved layers of a material 30 which exhibits relatively low radiation attenuation characteristics. Preferably, for computer-assisted tomographic purposes, the relatively high radiation attenuation material is tantulum which has a high density of approximately seventeen gm/cm³ and good machining properties, the relatively low radiation attenuation material comprising a substance such as air or acetate. As is illustrated in FIG. 6, rays moving in the desired direction, i.e. parallel to the arrow depicting the required path, will pass through the low absorption material 30, while diverging rays will be required to pass through long geometric paths of multiple layers of high absorption material 28. The drop in intensity of the forward beam due to the thickness of the absorbing layer 28 is a simple geometric relation in accordance with the following equation:

$$I = I_0 (b/t + b) \qquad 2$$

wherein I is the intensity after passage through the material;

$I_0$ is the intensity incident upon the material;

$t$ is the thickness of the sheet or layer of the absorbing material 28; and $b$ is the thickness of the sheet or layer of the spacing material 30 of low attenuating characteristic.

The total attenuation of the forward directed beam will be given by:

$$I = I_0 (b/t + b) (e^{-\mu a}) \qquad 3$$

wherein $a$ is the overall length of the collimator; and $\mu$ is the attenuation coefficient of the low attenuating characteristic spacing material.

With the collimator design of the instant invention, it is to be noted that the beam divergence is not determined by the overall width of the beam but rather by the length and separation of the layered sandwiched collimator. In this respect, beam divergence $\theta$ is given by:

$$\theta = \arctan (b/a) \qquad 4$$

where $a$ is the length of the absorbing material; and $b$ is the width of the separation or spacing material.

Figure 7:
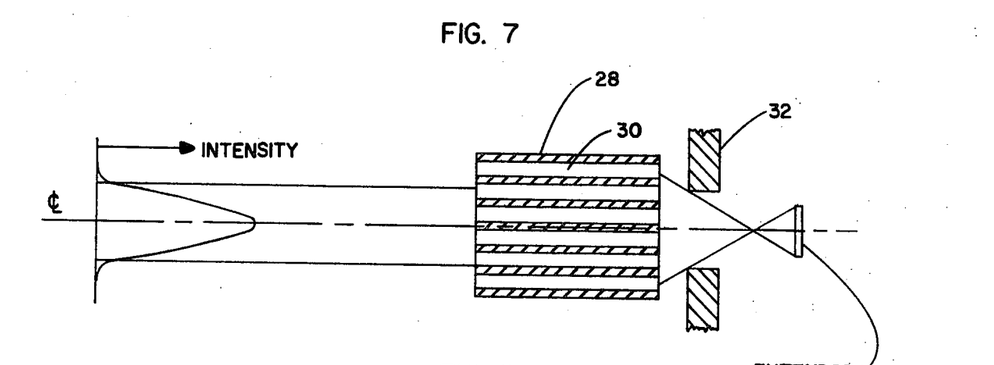
FIG. 7 is a schematic illustration of one preferred embodiment of the collimator design of the instant invention graphically illustrating the resulting beam intensity obtained from an extended or line source of radiation.

In practice, the sandwich assembly comprising the plurality of interleaved layers of material is contemplated to be placed adjacent a single slit aperture of radiation absorbing material 32 as is shown in both FIGS. 6 and 7 of the application drawings. It is to be appreciated that a plurality of layers of the sandwich assembly are provided for the single beam exiting from the slit in material 32, the sandwich assembly being disposed lengthwise along the desired direction of beam travel and oriented between the source and the target such the the attenuating layers 28 are parallel to the desired direction of the beam, with the interleaved spacing layers therefore providing direct paths for the radiation. Importantly, the resulting or emerging beam exiting from the collimator of the instant invention as is shown in FIG. 7 of the application drawings, exhibits substantially no divergence in at least one desired direction, even from an extended radiation source. The beam incident upon the target is sharply defined and in this instance has an approximately Gaussian intensity profile.

The specific geometrical configuration of the novel collimator design of the instant invention therefore constitutes a marked improvement over prior-art collimator approaches, as is evidenced by the resulting beam intensity and the lack of beam divergence. A better appreciation of the advantages to be gained through the utilization of the sandwich assembly collimator of the instant invention as contrasted with prior-art collimator approaches can be obtained from the following calculations, taken with typical dimensions as exist with respect to prior-art collimator assemblies and as is proposed as concerns the collimator device of the instant invention.

Figure 8:
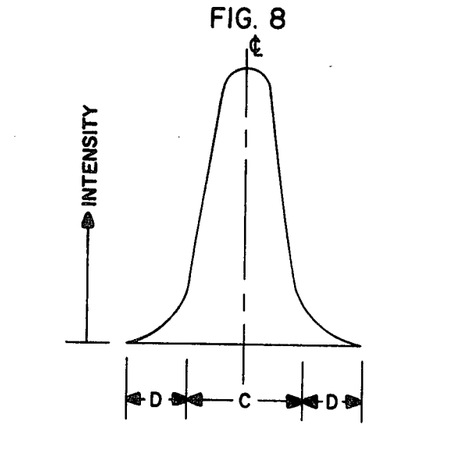
FIG. 8 is a graphical representation of the substantially Gaussian intensity of the resulting beam obtained from the collimator design of the instant invention.

In this respect, and dealing first with the collimator device of the instant invention, if it be assumed that the source of radiation is that which is obtained from a 130kv X-ray generator, the thickness of the attenuating or absorbing layers such as tantulum 28 could be 0.001 inches (dimension $t$), the thickness of the spacing or non-absorbing material 30 could be 0.020 inches (dimension $b$), and the length of the assembly (dimension $a$) could be 1.6 inches. Under such circumstances, the beam divergence $\theta$ would be 0.716° or 0.1025 radians. At a distance to the target of 40 inches, for example, the dimension D of the graphical intensity profile depicted in FIG. 8 would be 0.5 inches on each side of the initial aperture defined boundary represented by dimension $c$ in the schematic representation of FIG. 6, the initial aperture width $c$ utilized herein being 1.0 inches. As is clearly indicated in FIG. 8, the beam intensity profile is quite sharply defined and will be approximately Gaussian for the illustrated source.

Figure 9:
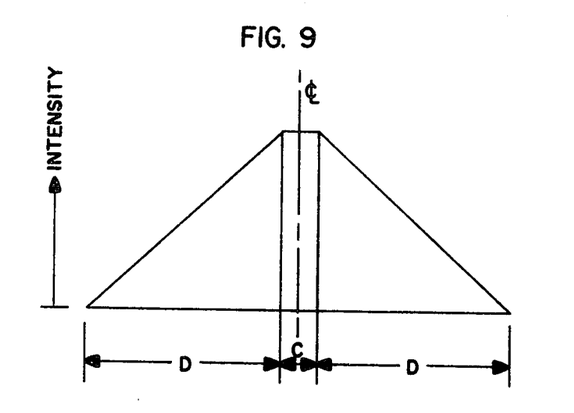
FIG. 9 is a graphical representation of the resulting beam intensity obtained from a conventional collimator design much as is illustrated in FIG. 4 of the application drawings.

In contrast with prior-art collimator designs and particularly a typical design such as that depicted in FIG. 5 of the application drawings or equivalents thereof, it will be noted that the beam divergence obtained with the collimator device of the instant invention is considerably smaller and substantially non-existant. With a prior-art double aperture or extended slit collimator of the type depicted in FIG. 5, the performance is dependent on the source to collimator separation A. Such a collimator with the same collimator length $a$ as was assumed for dimension $a$ in FIG. 6, with the aperture opening $c$ being the same as the aperture opening $c$ in FIG. 6, and with A = 0, will have a divergence D as is illustrated in FIG. 9 of about 25 inches, such region being exposed to either side of the parallel projection of the collimator operative at a distance of 40 inches. One must directly compare this relatively unacceptable result with the divergence D of 0.5 inches for the sandwich type collimator design of the instant invention. Further, source to collimator distance with the inventive collimator does not substantially affect the performance characteristics, thus allowing a more compact design.

The collimator design of the instant invention further takes into consideration techniques whereby a minimum reduction in actual beam intensity ensues. In this respect, and as is known, beam intensity is dependent on the thickness of the absorbing layers 28, and the length $a$ and attenuation coefficients of the spacing material 30 is indicated in FIG. 6. If we again assume the provision of tantulum of 0.001 inch thickness as the absorbing material, and a width of the spacing material of 0.020 inches, the geometric loss of beam intensity is given by:

$$\frac{I}{I_o} = \frac{t}{t+b} = \frac{.001}{.021} = 4.8\% \quad 5)$$

The loss in intensity due to the interleaved material is given by:

$$\frac{I}{I_o} = e^{-\sum_k u_k \Delta x_k} \quad 6)$$

where $$\sum_k u_k \Delta x_k$$

is the summation over all the material in the direct beam path that serves to space the absorbing layers.

To achieve maximum transmission of the radiation beam, the geometry of the spacing material 30 should be such as to minimize the actual material in the beam path. Proper design of the spacing material geometry can be made such that the attenuation is uniform, though low. One example of such a preferred design is that which is depicted in FIG. 12 of the application drawings, this spacing geometry being contemplated for utilization with the collimator configurations of FIGS. 10 and 11. As indicated, the spacing material 30 is designed to contain cavities 34 of low absorption material such as air, with a configuration such that all the rays of the emerging X-ray beam travel the same beam path length through the actual spacing material.

The particular geometric configuration of the sandwich collimator assembly of the instant invention is not critical to effect the general results above-described, provided that the radiation absorbing material be disposed in the beam and parallel to the direction of the beam path. Thus, if a parallel, sheet profile beam is desired, the sandwich assembly would constitute a plurality of stacked and substantially parallel layers of alternating attenuation and spacing material, with each respective layer type being substantially uniform in length and in thickness, but, of course, with the thickness of the spacing layers being much greater than the thin attenuating layers.

On the other hand, if a circular beam pattern is desired, modifications to the specific geometry can be made, again maintaining the basic geometric criteria as above-discussed. In this respect, attention is directed to FIG. 10 of the application drawings wherein a circular beam pattern is produced through a plurality of substantially equally spaced concentric cylindrical layers of alternating attenuating 29 and spacing 30 material, with each respective layer type being substantially uniform in length and in thickness. In FIG. 11, the sandwich assembly in effect comprises a layer of attenuating material 28, with the spacing layer 30 being juxtaposed thereon and the assembly being rolled upon itself as a spiral, a circular beam pattern similarly being produced.

Figure 10:
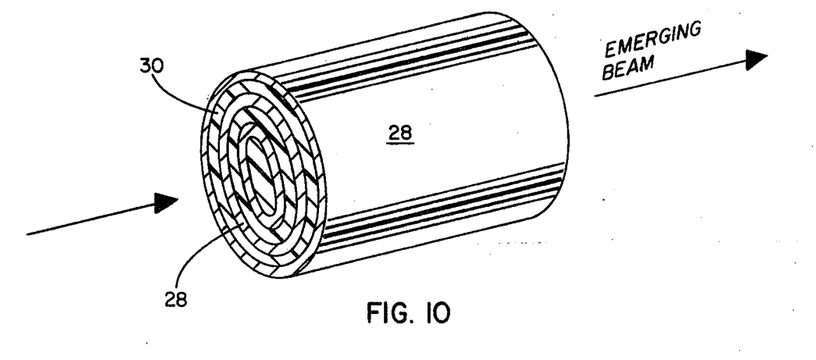
FIG. 10 depicts a further physical embodiment of the collimator design of the instant invention by which a circular beam pattern is obtained.
Figure 11:
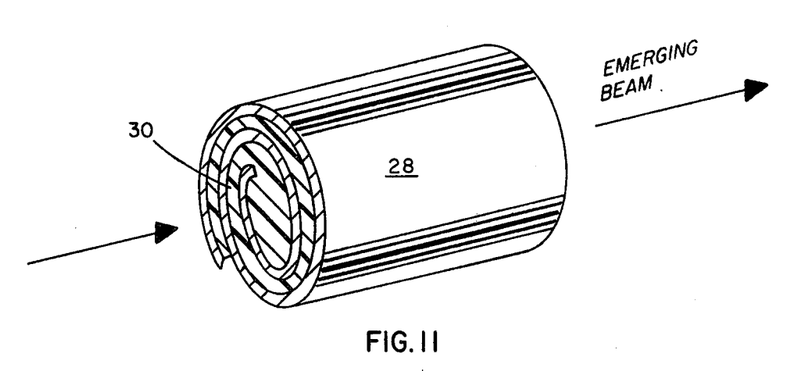
FIG. 11 is a perspective illustration of a variant of the embodiment of FIG. 10.
Figure 12:
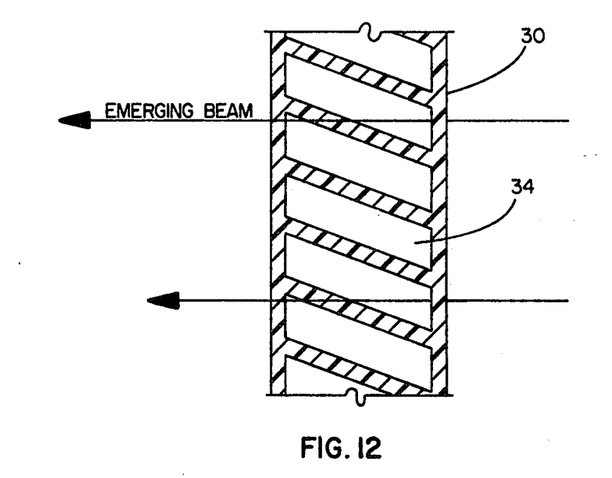
FIG. 12 is a top plan view depicting one specific and preferred geometric configuration of the relatively low attenuation material for utilization as a spacer in the collimator embodiments of FIGS. 10 and 11.
Figure 13:
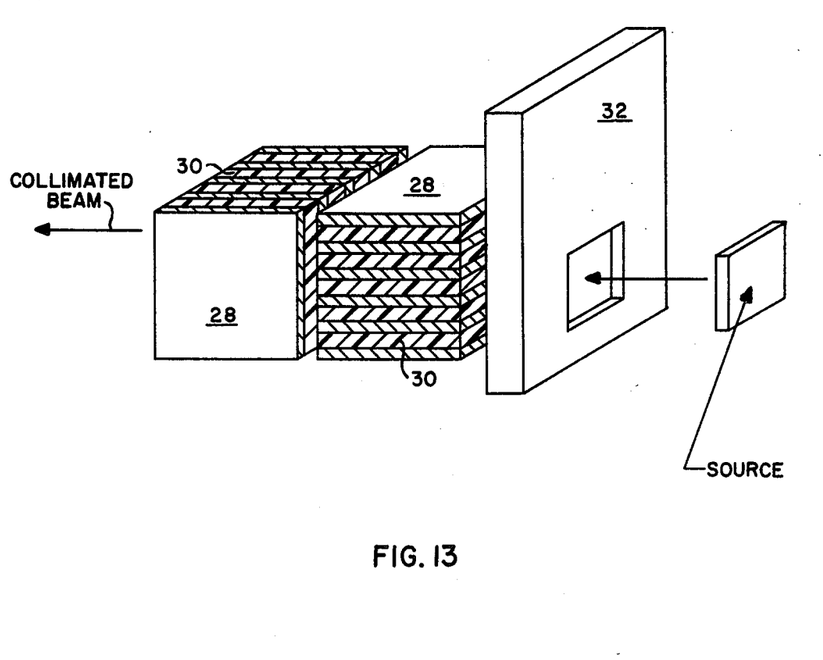
FIG. 13 is a perspective diagrammatic illustration of the basic geometry of FIG. 7 utilized for collimation in a two dimensional plane.

The geometric configurations of FIGS. 10 and 11, of course, produce a collimated and non-diverging beam in two directions or planes due to the circular, closed structure provided. On the other hand, the parallel stacked sheet sandwich assembly as schematically depicted in FIGS. 6 and 7 will provide a beam that is non-divergent in only one plane or direction as was discussed. If two dimensional non-divergence is desired, several sandwich assemblies could be provided in the fashion shown in FIG. 13, where like parts have been indicated by the same reference numerals. In FIG. 13, the two sandwich assemblies are disposed so that the respective parallel attenuating layers of each assembly are at right angles to the other, but with each assembly being longitudinally spaced in the direction of beam travel. Rather than so spacing the assemblies per se, the assemblies could actually be placed "inside" one another to form a single egg crate-like structure having a plurality of compartments defined by the perpendicularly disposed attenuating plates.

Within the basic teachings and principles of the invention, many other geometric modifications will be evident to those skilled in the art. Further, where plural beams are desired, a separate collimator assembly could be provided for each such beam, or if desired, one assembly of relatively larger dimensions could be utilized in conjunction with an array of initial apertures so as to provide multiple emerging beams.

As previously explained, the utilization of the collimator of the instant invention in conjunction with a radiation imaging device such as a computer-assisted tomographic scanning apparatus of the type depicted in FIG. 1 will provide a much improved apparatus in that radiation to the patient outside the area of interest, outside the thin "disc" or "slice", is virtually eliminated, and degradation of the image resolution due to scattering of divergent X-ray photons is minimized. It must be appreciated, however, that while a primary contemplated utilization of the collimator device of the instant invention is in association with X-ray diagnostic or imaging devices, the non-diverging nature of the beam exiting from the novel collimator can and is intended to find useful application elsewhere. Specifically, though not by way of limitation, the collimator could be utilized in therapeutic radiation devices, or in a receiving as well as transmitting operational mode.

It should be appreciated that the objectives set forth at the outset of this specification have been successfully achieved. Accordingly,

What is claimed is:

1. In a tomographic patient imaging apparatus of the type wherein photons emitted by a radiation source through an aperture means, the dimensions of which define a boundary of the desired beam to be projected, are caused to pass in a beam at different angles and directions through a thin slice or section of the patient and be at least partially attenuated and absorbed thereby, with the intensity of the emerging beam being detected and measured in a detector means so as to obtain signals representative of the absorption coefficients and density of the slice, said signals being manipulated by a computer whereat the image of said slice is reconstructed, said reconstructed image thereafter being displayed, the improvement of a collimating apparatus disposed adjacent the radiation source and defining means for projecting towards the patient a penetrating beam of radiation which is substantially non-diverging from said defined boundary in at least one direction to minimize radiation exposure to the patient outside the area of the selected thin slice, said collimating apparatus comprising an elongated sandwich assembly of a plurality of layers of material exhibiting relatively high radiation attenuation characteristics, said attenuating layers being spaced apart and separated from one another by interleaved layers of material exhibiting relatively low radiation attenuation characteristics, said sandwich assembly being disposed in a lengthwise manner adjacent the aperture means in the path and throughout the defined boundary of the radiation emitted through the aperture means, such that said attenuating layers are parallel to the desired direction of the projected beam with said interleaved spacing layers providing multiple direct paths for the radiation comprising the projected beam.

2. The improvement of claim 1, wherein "$a$" is the length of said sandwich assembly, "$b$" is the spacing between attenuating layers thereof, whereby the geometry of said sandwich assembly is such that the divergence $\theta$ of the projected beam in said at least one direction is substantially equal to arc tan $b/a$.

3. The improvement of claim 1, wherein said sandwich assembly comprises of plurality of stacked and substantially parallel layers of alternating attenuation and spacing material, each said respective layer being substantially uniform in length and in thickness but with the thickness of said spacing layers being greater than the thickness of said attenuating layers.

4. The improvement as defined in claim 1, wherein two sandwich assemblies are provided, said assemblies being further disposed so that said attenuating layers of one assembly are oriented at right angles to said attenuating layers of the other assembly.

5. The improvement as defined in claim 1, wherein said material of said interleaved spacing layer contains low absorption cavities therein disposed in a predetermined geometric configuration such that all the rays of the emerging beams travel the same beam path length through said relatively low attenuation characteristic material of said spacing layer.

6. The improvement as defined in claim 1, wherein said sandwich assembly comprises a plurality of substantially equally spaced concentric cylindrical layers of alternating attenuation and spacing material, each said respective layer type being substantially uniform in length and in thickness, whereby a circular beam pattern is produced.

7. The improvement as defined in claim 1, wherein said sandwich assembly comprises a layer of attenuating material with a spacing layer juxtaposed thereon, said assembly being rolled upon itself as a spiral, whereby a substantially circular beam pattern is produced.

8. The improvement as defined in claim 1, wherein said relatively high attenuating material comprises tantulum.

9. The improvement as defined in claim 1, wherein said relatively high attenuating material comprises lead.

* * * * *